United States Patent
Moon et al.

(10) Patent No.: US 10,017,462 B1
(45) Date of Patent: Jul. 10, 2018

(54) ANTIMICROBIAL POLY(GUANYLUREA)S

(71) Applicants: Joong Ho Moon, Weston, FL (US); Md Salauddin Ahmed, Comilla (BD)

(72) Inventors: Joong Ho Moon, Weston, FL (US); Md Salauddin Ahmed, Comilla (BD)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/911,299

(22) Filed: Mar. 5, 2018

(51) Int. Cl.
*C08G 73/06* (2006.01)
*C07C 279/24* (2006.01)
*C07D 241/04* (2006.01)
*C08G 71/02* (2006.01)

(52) U.S. Cl.
CPC .......... *C07C 279/24* (2013.01); *C07D 241/04* (2013.01); *C08G 71/02* (2013.01)

(58) Field of Classification Search
CPC ...... C07C 279/24; C07D 241/04; C08G 71/02
See application file for complete search history.

(56) References Cited

PUBLICATIONS

Bass et al., ChemMedChem, 2017, 12, 288-291.*

* cited by examiner

*Primary Examiner* — Shane Fang
(74) *Attorney, Agent, or Firm* — Saliwanchik, Lloyd & Eisenschenk

(57) ABSTRACT

A poly(guanylurea) (PGU), comprising the structure where a multiplicity of repeating units are connected by guanylurea groups. The repeating units comprise: linear or cyclic alkylene, heteroatom interrupted alkylene, cycloalkylene, arylene, or heteroarylene; and a linear or cyclic alkylene, one or more heteroatom interrupted alkylene, cycloalkylene, arylene, heteroarylene, or a dinitrogen heterocycle. The PGU can be used as an antimicrobial agent with low toxicity in a pharmaceutical composition, generally as a protonated PGU upon combining with a pharmaceutically acceptable acid.

13 Claims, 8 Drawing Sheets

ANTIMICROBIAL POLY(GUANYLUREA)S

This invention was made with government support under DMR1352317 awarded by the National Science Foundation. The government has certain rights in the invention.

BACKGROUND OF INVENTION

Antimicrobial drug resistance has emerged rapidly and thwarted most treatment options, leading to prolonged illness, disability, and death. Despite considerable efforts to develop new antimicrobial drugs, many bacterial infections remain difficult to treat due to acquired drug resistance. Compared to small molecular antibiotics designed to interrupt the bacterial intracellular biochemical processes, antimicrobial polymers target the disruption of membrane integrity, offering a promising strategy to overcome drug resistance. Bacteria have little chance of developing a resistance mechanism against the physical disruption, which often leads to cell death.

The design principle of antimicrobial polymers has been focused primarily on balancing positive charges with the hydrophobicity in the pendant side chains in order to achieve selective disruption of the bacterial membrane over the mammalian cell membranes. By polymerizing various monomers containing positively charged hydrophobic side chains, many polymers with different functionalities and architectures have been developed and demonstrated for antimicrobial activities against a broad spectrum of bacterial species. Although current synthetic approaches have proven capable of developing highly selective antimicrobial polymers, a simple synthetic method for developing antimicrobial polymers with improved biocompatibility, selectivity, and specificity is needed.

Similar to facially structured host defense antimicrobial peptides (AMPs), antimicrobial polymers are attracted by the envelope components, transferred to the bacterial membrane, and adopt amphiphilic conformations necessary for disrupting the membrane. Recent molecular dynamic simulations suggest that the randomly distributed and oriented polymer side chains are reorganized into ordered amphiphilic chain architectures upon interacting with the negatively charged bacterial membrane. To this end, the design and development of polymers that favor the membrane disruption processes by compensating for the thermodynamic entropy loss upon forming ordered structures with enthalpy gains due to ionic, hydrophobic, and hydrogen-bonding (H-bonding) interactions are desired.

BRIEF SUMMARY

Embodiments of the invention are directed to a poly(guanylurea) (PGU), having the structure:

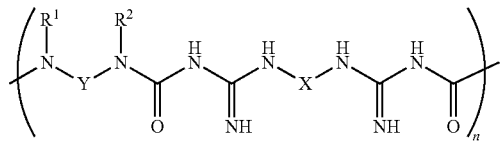

or any protonated or plurally protonated salt thereof. The PGU is a polymer where n is 3 to 100. Repeating units comprising X are linear or cyclic alkylene, heteroatom interrupted alkylene, cycloalkylene, arylene, heteroarylene, or a combination thereof. Repeating units comprising Y are linear or cyclic alkylene, one or more heteroatom interrupted alkylene where the herteroatom is O, S, NH, or a combination thereof, cycloalkylene, arylene, heteroarylene, or a combination thereof. Groups $R^1$ and $R^2$ are independently, H, substituted or unsubstituted linear, branched, or cyclic alkyl, one or more heteroatom interrupted substituted or unsubstituted linear branched or cyclic alkyl where the herteroatom is O, S, NH or a combination thereof, unsubstituted or substituted aryl, substituted or unsubstituted heteroarylene. Alternatively, $R^1$ and $R^2$ are combined as an alkylene or heteroatom interrupted alkylene, where $R^1NYNR^2$ comprises a dinitrogen heterocycle, and where substituents are $C_1$ to $C_{20}$ alkyl, $C_1$ to $C_{20}$ alkoxy, hydroxyl, $C_1$ to $C_{20}$ acyl, $C_1$ to $C_{20}$ acyloxy, amino, $C_1$ to $C_{20}$ alkyl amino, $C_1$ to $C_{20}$ dialkylamino, $C_1$ to $C_{20}$ acylamino, $C_2$ to $C_{20}$ acylalkylamino, fluoro, chloro, bromo, iodo, mercapto, $C_1$ to $C_{20}$ alkylthio, $C_6$ to $C_{18}$ aryl, $C_6$ to $C_{18}$ aryloxy, $C_6$ to $C_{18}$ arylamino, $C_6$ to $C_{32}$ diarylamino, or $C_7$ to $C_{38}$ alkylarylamino. The PGU can include one or more tert-butyloxycarbonyl protecting group (BOC).

Another embodiment of the invention is directed to a method of making the PGU, described above. The method involves combining first monomers with X as a di-terminal Boc-protected guanidine groups terminal to a linear or cyclic alkylene, heteroatom interrupted alkylene, cycloalkylene, arylene, heteroarylene, or a combination thereof, with second monomers with Y that has terminal ends that are an isocyanate or a dinitrogen heterocycle with a carbonate or amines of a diamine capped linear or cyclic alkylene, one or more heteroatom interrupted alkylene where the herteroatom is O, S, NH, or a combination thereof with the carbonate. The polymerization mixture is then heated to form the PGU. The carbonate can be alkali metal carbonate.

Another embodiment of the invention is directed to a pharmaceutical composition comprising the PGU. The pharmaceutical composition can be use as an antimicrobial agent.

DETAILED DISCLOSURE

Figure 1:
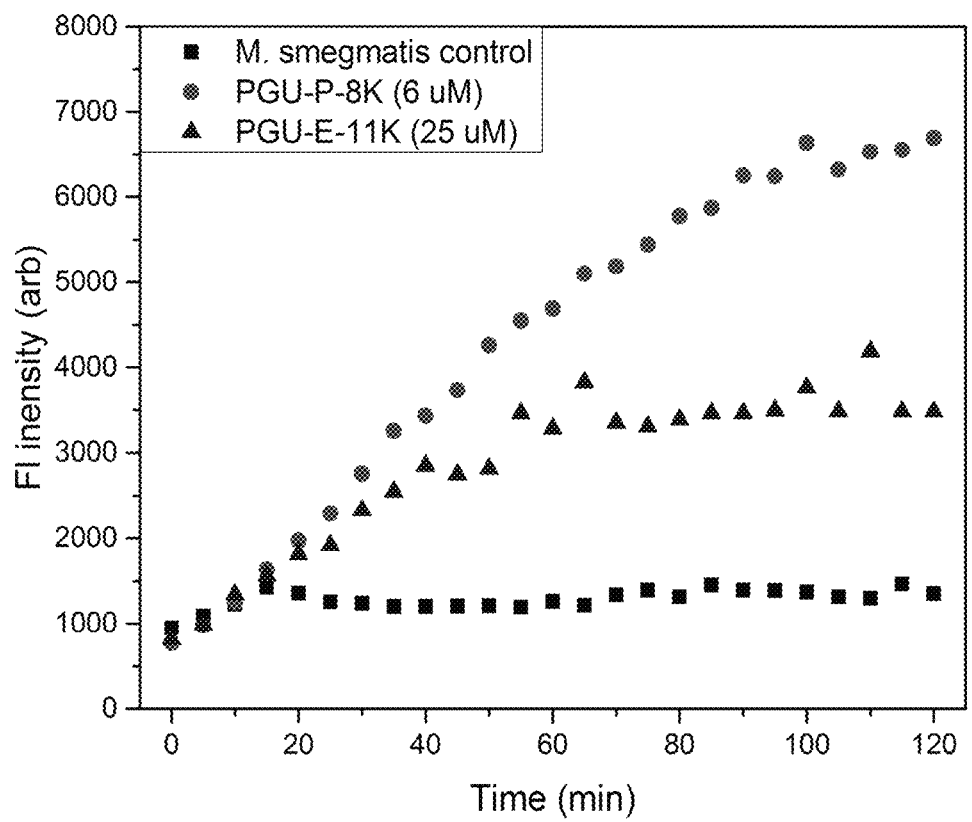
FIG. 1 shows plots of the rate of membrane permeation and nucleic acids intercalation for control EB (rectangles) and various PGU-treated cells, according to embodiments of the invention, (circles and triangles), which allow high EB internalization caused by the membrane disruption of *M. smegmatis* as indicated by fluorescence.
Figure 2A:
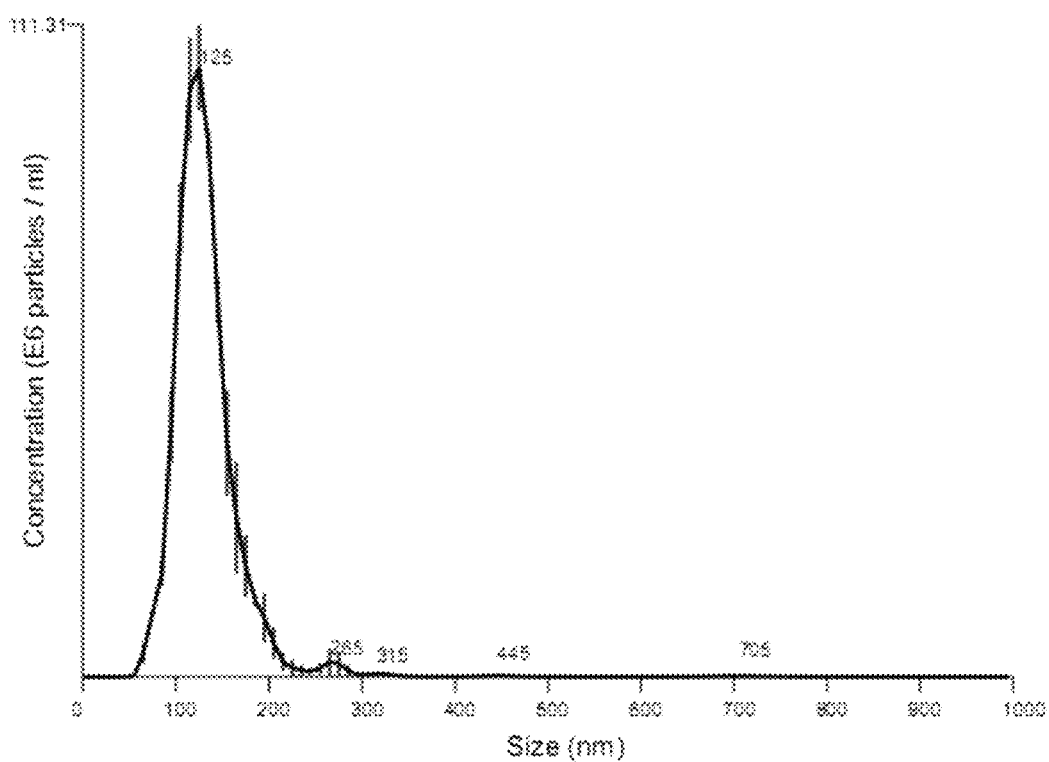
FIG. 2A shows a plot of the hydrodynamic diameter of PGU-P-14K, according to an embodiment of the invention, in 7H9 medium.
Figure 2B:
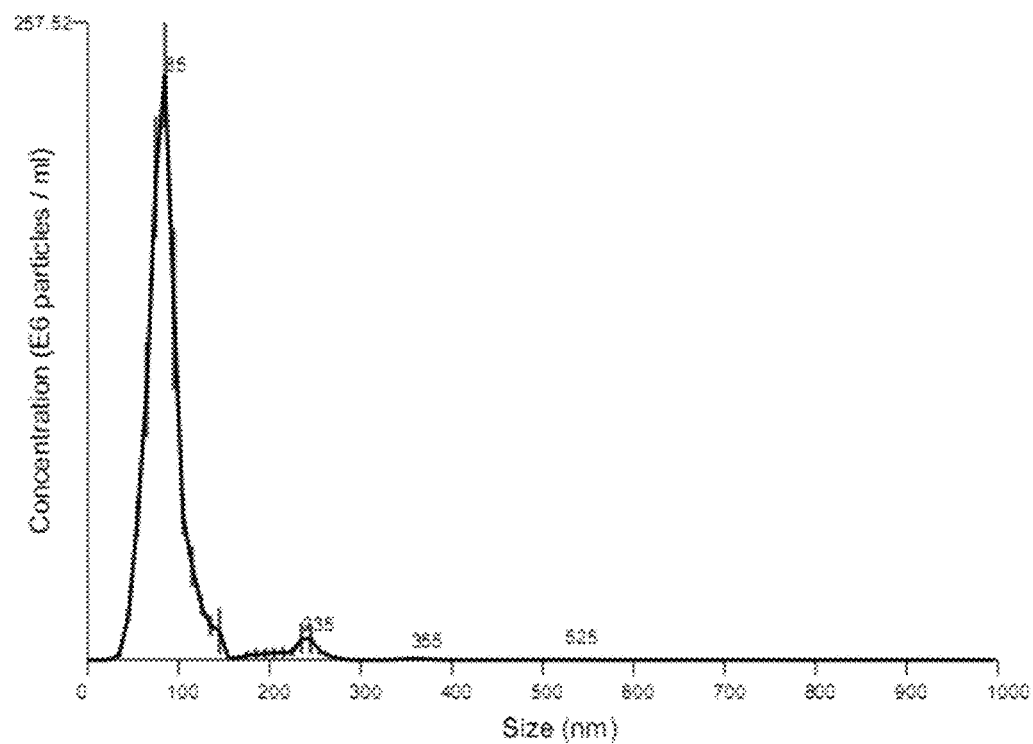
FIG. 2B shows a plot of the hydrodynamic diameter of PGU-P-8K, according to an embodiment of the invention, in 7H9 medium.
Figure 2C:
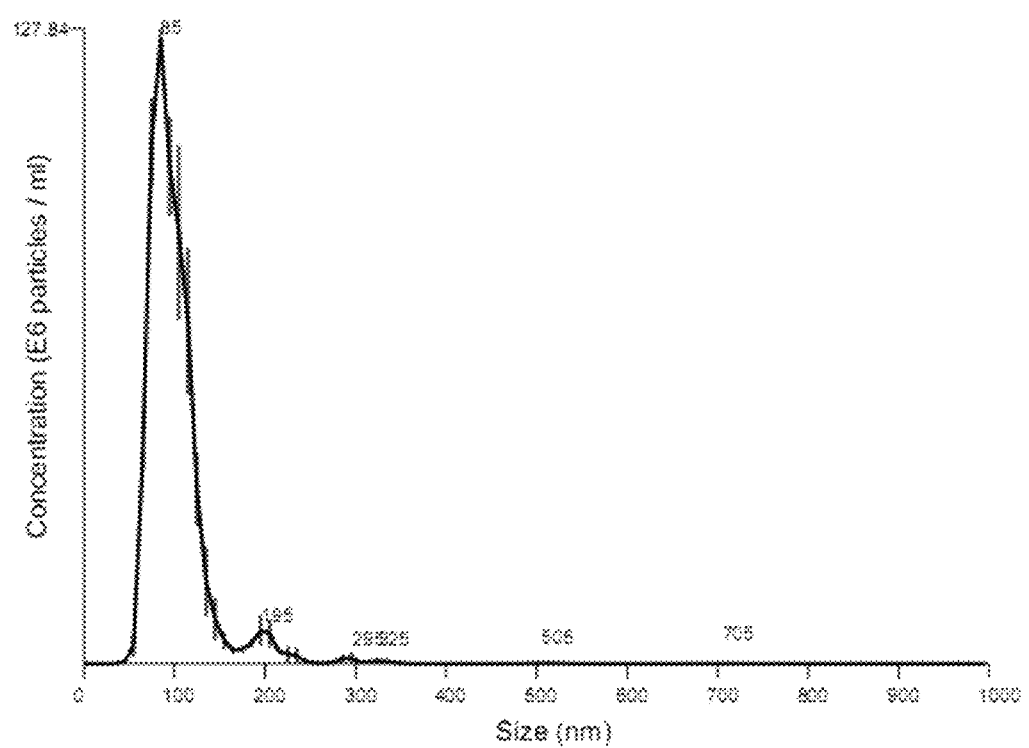
FIG. 2C shows a plot of the hydrodynamic diameter of PGU-P-3K, according to an embodiment of the invention, in 7H9 medium.
Figure 2D:
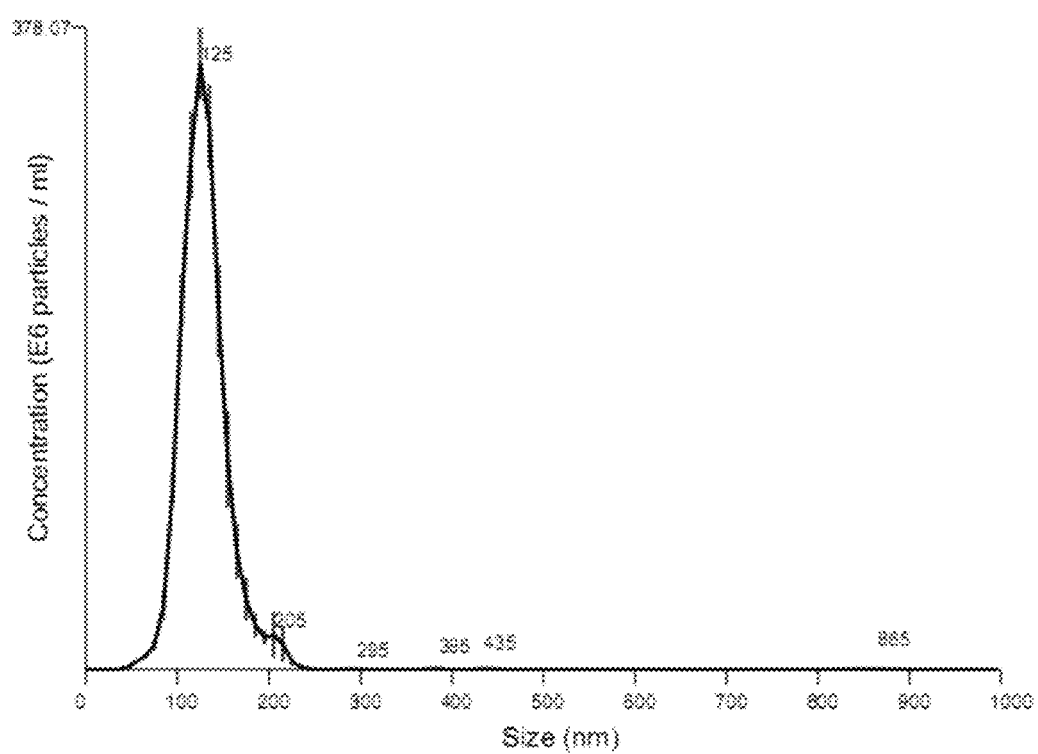
FIG. 2D shows a plot of the hydrodynamic diameter of PGU-E-11K, according to an embodiment of the invention, in 7H9 medium.
Figure 2E:
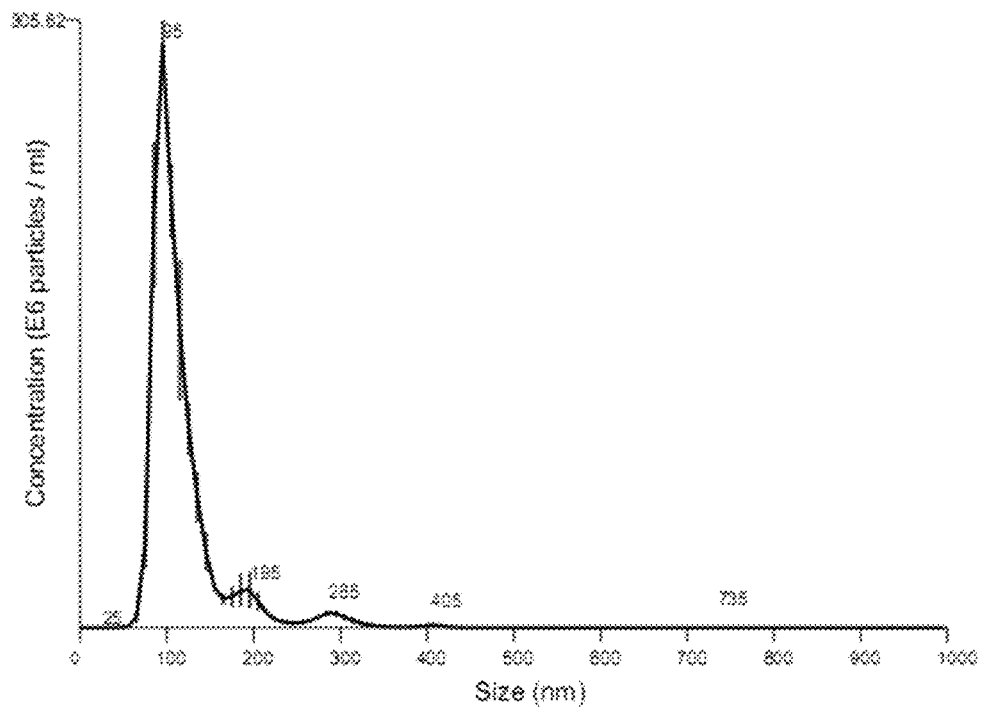
FIG. 2E shows a plot of the hydrodynamic diameter of PGU-E-7K, according to an embodiment of the invention, in 7H19 medium.
Figure 3A:
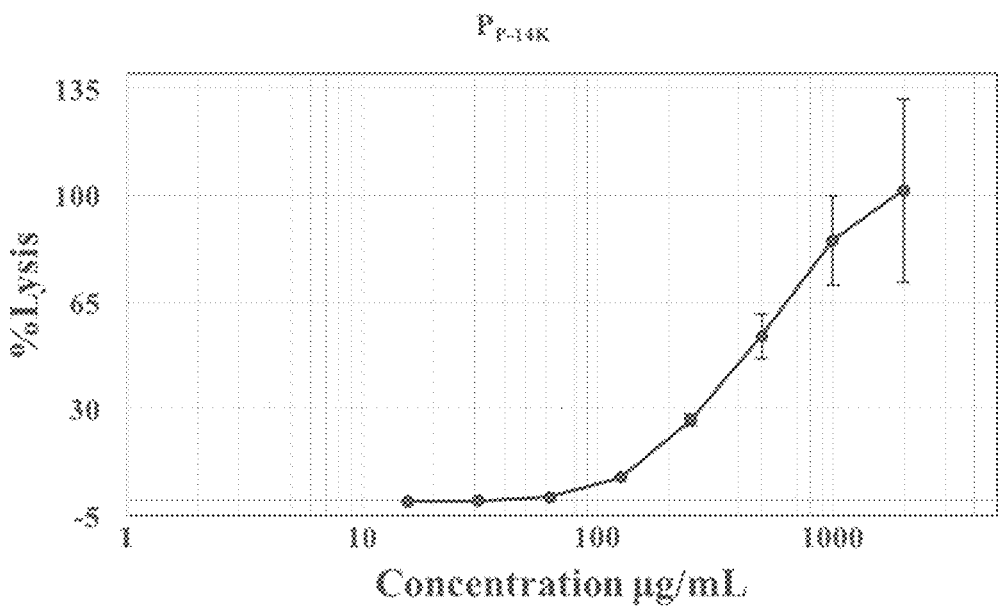
FIG. 3A shows a plot of the $HC_{50}$ for PGU-P-14K, according to an embodiment of the invention.
Figure 3B:
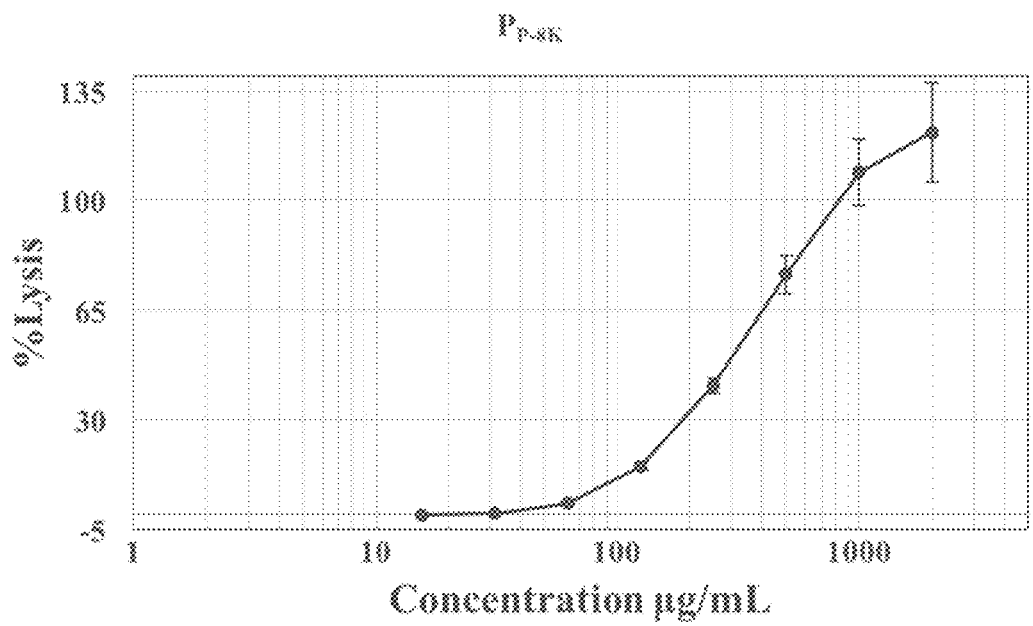
FIG. 3B shows a plot of the $HC_{50}$ for PGU-P-8K, according to an embodiment of the invention.
Figure 3C:
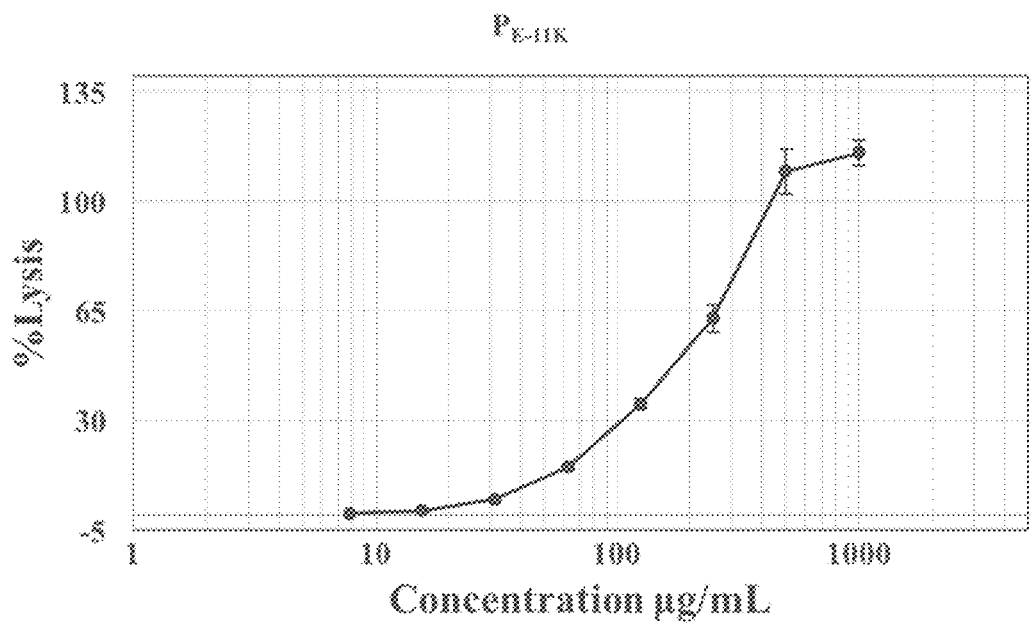
FIG. 3C shows a plot of the $HC_{50}$ for PGU-E-11K, according to an embodiment of the invention.
Figure 3D:
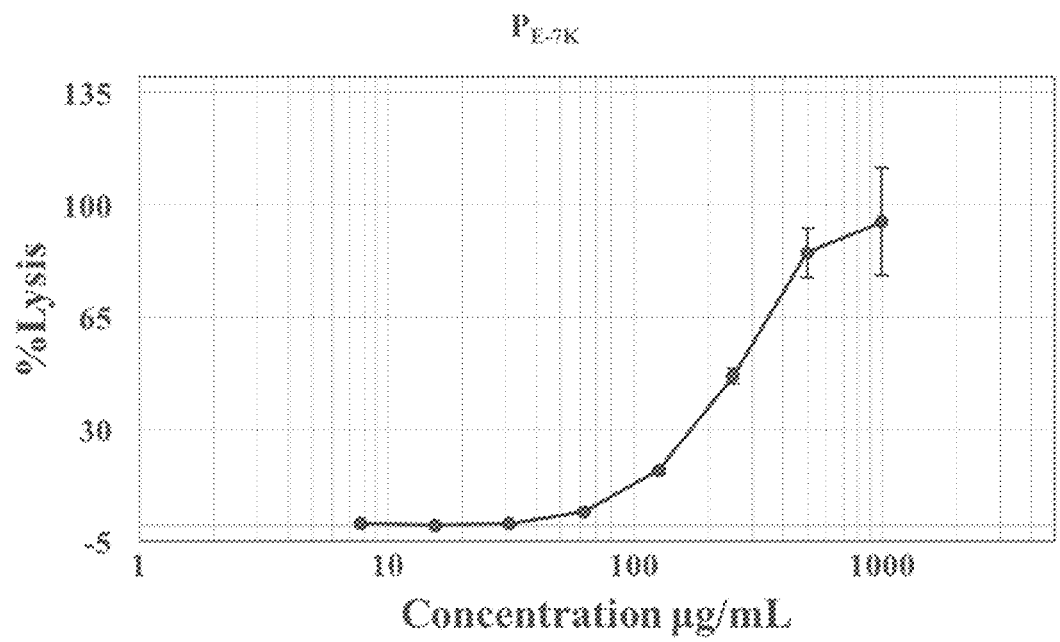
FIG. 3D shows a plot of the $HC_{50}$ for PGU-E-7K, according to an embodiment of the invention.

Embodiments of the invention are directed to a new class of polymers, poly(guanylurea)s (PGUs), containing a guanylurea backbone capable of ionic, hydrophobic, and H-bonding interaction with bacterial cell membranes are illustrated below in an unprotonated and a highly protonated form:

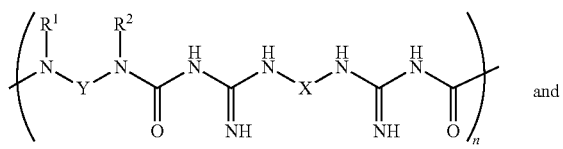

and

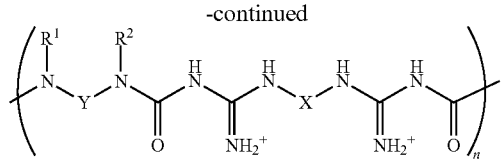

where X is linear or cyclic alkylene, heteroatom interrupted alkylene, cycloalkylene, arylene, heteroarylene, or a combination thereof, Y is linear or cyclic alkylene, heteroatom interrupted alkylene, cycloalkylene, arylene, heteroarylene, or a combination thereof, and $R^1$ and $R^2$ are independently, H, alkyl, substituted alkyl, heteroatom interrupted alkyl, aryl, substituted aryl, heteroarylene, or $R^1$ and $R^2$ are combined as an alkylene or heteroatom interrupted alkylene, where $R^1NYNR^2$ comprises a heterocycle. It should be understood that the positive charges of the protonated form are balanced by an anion, that may be a where protonation is from a carboxylic acid, a mineral acid, or any pharmaceutically acceptable organic or inorganic acid.

Preparation of the PGUs is shown in Scheme 1 and Scheme 2, below. In contrast to copolymers where high entropy loss due to significant structural transformation from highly randomized side chain and backbone structures to relatively ordered orientations; the new polymers introduce positive charge and hydrophobicity into the polymer backbones. The polymer backbone may be positively charged. With a large positive charge density per repeating unit, various hydrophobic/hydrophilic units can be introduced to balance the amphiphilicity of the polymer. In order to achieve an additional enthalpy gain, a novel guanylurea functional group is an H-bond donor and an H-bond acceptor resides within the positively charged polymer backbone. The guanylurea functional group is a product of guanidine and urea. Although low molecular weight synthetic compounds and naturally occurring peptides that contain guanylurea derivatives show activity against bacteria, fungi, and viruses, the PGUs according to embodiments of the invention, are more biocompatible than most synthetic antimicrobial polymers, which encounter difficulties in in vivo applications.

Scheme 1

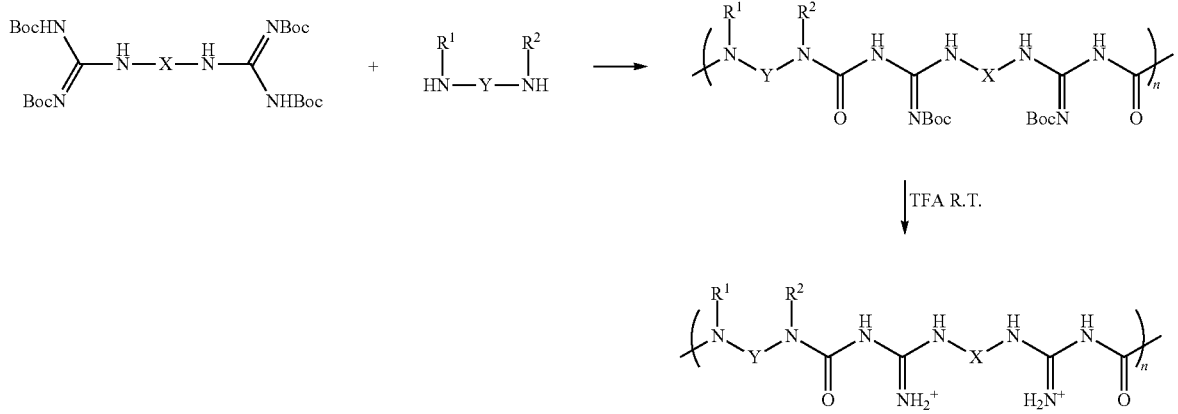

Scheme 2

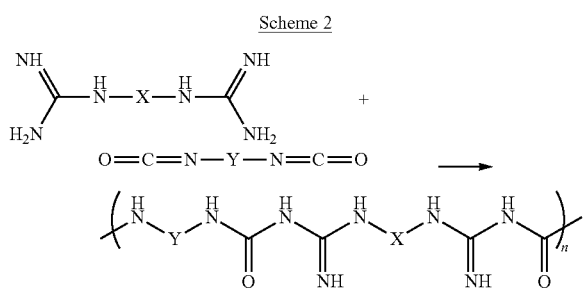

Poly(guanylurea piperazine)s (PGU-Ps), according to an embodiment of the invention, are synthesized by reacting piperazine with a monomer containing t-butyloxycarbonyl (Boc)-protected guanidine groups at the end of a short ethylene oxide side chains, monomer A, as indicted in Scheme 1. The monomer's aryliodide group provides hydrophobicity. The hydrophobic aryliodide units induce polymer chains to aggregate into nanoparticles (NPs) in bacteria culture medium. Piperazine creates rigidity between two guanylurea groups. The backbone rigidity and planarity is a synthetic mimic of AMPs, and play important roles in antimicrobial activity because of favorable membrane interaction. Acyclic ethylenediamine is prepared as a control poly(guanylurea ethylenediamine) (PGU-E) that lacks the rigidity at the charge sites. Positively charged PGUs are polymerized via guanylurea bond formation. Positively charged PGUs are not water soluble, but highly soluble in DMSO. PGU dissolved in DMSO placed into a bacterial culture medium [e.g., Mueller-Hinton Broth (MHB) and 7H9], forms NPs with a narrow size distribution. For example, the hydrodynamic diameters (HDs) of PGU-P an PGU-E with molecular weights of 8,000 (i.e., PGU-P-8K) and 7,000 g/mol (i.e., PGU-E-7K) in 7H9 medium form nanoparticles of 86±1.9 and 106±5.8 nm, respectively, by nanoparticle tracking analysis in triplicates of three independent samples (Supporting Information). Zeta potentials measurements suggest that the NPs formed in MHB (and 7H9) are polymer-protein complexes. While no zeta potentials were obtained from control MHB (i.e., no PGUs), PGUs in both media exhibit zeta potentials in the range of −14 to −17 mV.

Assays conducted to evaluate potential toxicity toward mammalian cells are MTT and hemolysis assay indicate that PGUs with different molecular weights exhibit ignorable cell viability inhibition when human cervical carcinoma cells (HeLa) upon incubation with various amounts of polymers overnight. The MTT assay for the metabolic activity of live cells uses color change of a tetrazolium dye [3-(4,5-dimethylthiazol-2-yl)-2,5-diphenyltetrazolium bromide]. Using human red blood cells (RBCs), the hemolytic activities of PGUs require polymer concentrations required for 50% of hemolysis ($HC_{50}$), as determined by measuring the amounts of hemoglobin released from RBCs due to the membrane damage, is provided in Table 1, below. As shown in Table 1, all PGUs are relatively nontoxic to RBC. PGU-Ps exhibit substantially lower hemolytic activity than PGU-Es, indicating that rigidity along the backbone is an important structural factor affecting the hemolytic activity. Because mammalian cell membranes contain hydrophobic cholesterols and phosphatidylcholine, increasing the hydrophobicity in an antimicrobial polymer often increases hemolytic activities. PGUs that have the slightly increased hydrophobicity due to incorporation of piperazine rather substantially decreases hemolytic activity, indicating that the reduced cytotoxicity of PGU-Ps is related to the rigidity between charged guanylurea groups.

TABLE 1

Antimicrobial and hemolytic activities of poly(guanylurea)s (PGUs).

| | MIC (μg/mL) | | | | | Selectivity ($HC_{50}$/MIC) | | | |
|---|---|---|---|---|---|---|---|---|---|
| PGU | M. smegmatis | S. flexneri | MRSA | S. aureus | $HC_{50}$ (μg/mL) | M. smegmatis | S. flexneri | MRSA | S. aureus |
| P-14K | 6.5 | 25.5 | 25.5 | 13 | 504 | 77.5 | 19.8 | 19.8 | 38.8 |
| P-8K | 3.1-6.5 | 25.5 | 13 | 13 | 394 | 60.6-126 | 15.4 | 30.3 | 30.3 |
| P-3K | 102 | >203 | >203 | >203 | >2000 | >19.6 | >9.9 | >9.9 | >9.9 |
| E-11K | 25 | 25-50 | 99 | 99 | 232 | 4.6-9.0 | 6.0 | 2.3 | 2.3 |
| E-7K | 50-99 | 198 | 198 | 198 | 257 | 2.6-5.0 | 1.3 | 1.3 | 1.3 |

Antimicrobial activities of various molecular weight PGUs against *Mycobacterium smegmatis* (a *mycobacterium*), *Staphylococcus aureus* (a Gram-positive bacterium), methicillin-resistant *Staphylococcus aureus* (MRSA), and *Shigella flexneri* (a Gram-negative bacterium) as evaluated by the minimal inhibitory concentrations (MIC) is also shown in Table 1, above. The PGU-Ps function well against these bacteria. PGU-P-8K exhibits the highest efficiency against *M. smegmatis* (3.1-6.5 μg/mL), implying that the mechanism of PGU-Ps is associated with membrane disruption. A hallmark of the host defense AMPs and their synthetic mimics is nonspecific antimicrobial activity against a broad spectrum of bacterial species due to the nonspecific membrane disruption mechanism. Among the tested bacteria, MIC values against *Shigella flexneri* are higher than other types of bacteria, presumably due to the presence of the additional outer membrane of the Gram-negative bacteria. While the MIC values of PGU-P-8K and -14K are relatively comparable, low molecular weight (3,000 g/mol) PGU-P-3K exhibits poor antimicrobial activity, presumably due to the greatly reduced electrostatic and H-bonding interactions between the low molecular weight oligomer and the negatively charged membrane.

The effect of backbone rigidity on antimicrobial activity is apparent from the behavior of PGU-Es with comparable molecular weights (e.g., 11,000 and 7,000 g/mol) to those of PGU-Ps, with their MIC and $HC_{50}$ measured under identical tested condition. As shown in Table 1, above, MIC values of PGU-Es increase sharply and $HC_{50}$ values increase about 2-fold when the two guanylurea groups along the backbone were coupled by the ethylene group. This structure-activity relationship suggests that the rigid connection of two positively charged planar guanylurea groups plays an important role in selective disruption of the bacteria over mammalian membranes. In general, PGU-Ps exhibit good selectivity, as defined by the ratios $HC_{50}$/MIC across the tested bacteria when compared to PGU-Es. Specifically, the effect of rigidity on antimicrobial activity and selectivity were most pronounced on *M. smegmatis*. The antimicrobial activity and selectivity of PGU-P-8K against *M. smegmatis*, as indicated in FIG. 1, are enhanced by about 16- and 14-fold, respectively, when compared to similarly sized PGU-E-7K. PGU-E-11K, which exhibit moderate activity against *M. smegmatis* and display no activity toward other types of bacteria.

A membrane permeability assay using ethidium bromide (EB) was conducted. Non-fluorescent EB becomes fluorescent upon permeation through the membranes and the subsequent intercalation into intracellular nucleic acids. Due to tight regulation of the membrane permeability and the efflux pumps, fluorescence intensity of normal bacteria cells treated with EB is generally low. However, damaged membranes allow increased intracellular diffusion of EB and/or the efflux pumps are inhibited, i.e., reducing the pump drainage efficiency, as indicated by the increased fluorescence intensity of bacterial cells. Fluorescence intensities of bacteria cells treated with PGUs at MIC values over 2 h show an increased fluorescence intensity of control *M. smegmatis* over the initial 20 min of EB incubation and then plateaus, as shown in FIG. 1. This indicates that *M. smegmatis* tightly controls the amount of intracellular EB by balancing the influx and outflow of EBs. At the MICs, fluorescence intensities of *M. smegmatis* treated with PGU-P-8K (circles) and PGU-E-11K (triangles), respectively, were substantially increased, supporting the membrane disruption mechanism of PGUs. After two-hour incubation, PGU-P-8K induces higher membrane permeability, probably due to membrane damage, than does PGU-E-11K, judged on their relative fluorescent intensities. Similar fluorescence patterns are observed from Gram-negative *Shigella flexneri* incubated with PGU-P-8K and PGU-E-11K, although the level of membrane damage determined by the fluorescence intensity within two hours of incubation is lower than that of *M. smegmatis*. Even though PGU-P-8K exhibiting better antimicrobial efficiency (MIC 13 μg/ml) against MRSA than a widely used antibiotic Ciprofloxacin (MIC 20 μg/ml), the EB assay result obtained within two hours of incubation is not informative, as no similar patterns of fluorescence intensity changes were correlated to the amounts and types of PGUs.

The PGUs, according to embodiments of the invention, can be provided separately or in combination as medicaments that antibacterial, antiviral, antifungal, or any combination thereof. The medicaments can be formulated according to known methods for preparing pharmaceutically useful compositions. Such pharmaceutical compositions can be adapted for various forms of administration, such as, but not limited to, oral, parenteral, nasal, topical, and transdermal. The PGUs can be provided as solutions, amorphous compounds, injectables, pills, inhalants, or in any other form for administration. The PGUs can include a pharmaceutically acceptable carrier or diluent. Formulations are described in a number of sources, which are well known and readily available to those skilled in the art. For example, *Remington's Pharmaceutical Science* (Martin EW [1995] Easton Pa., Mack Publishing Company, 19$^{th}$ ed.) describes formulations that can be used in connection with embodiments of the invention. Formulations suitable for administration include, for example, aqueous sterile injection solutions, which may contain antioxidants, buffers, bacteriostats, and solutes, which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, or tablets of the PGU comprising compositions. It should be understood that in addition to the ingredients particularly mentioned above, the formulations of the subject invention can include other agents conventional in the art having regard to the type of formulation in question.

Pharmaceutically acceptable carriers used in PGU formulations include, but are not limited to, inert diluents and vehicles such as: one or more excipients, buccal tablets, troches, capsules, elixirs, suspensions, syrups, wafers, and aerosol sprays. Tablets, troches, pills, capsules, and the like may, but do not necessarily, contain binders, such as gum tragacanth, acacia, corn starch or gelatin; excipients, such as dicalcium phosphate; a disintegrating agent, such as corn starch, potato starch, or alginic acid; a lubricant, such as magnesium stearate; a sweetening agent, such as sucrose, fructose, lactose or aspartame; flavoring agent, such as peppermint, oil of wintergreen, or cherry flavoring; a liquid carrier, such as a vegetable oil or a polyethylene glycol; and/or solid carriers; such as finely divided solids such as talc, clay, microcrystalline cellulose, silica, or alumina. Any material used in preparing the dosage form should be pharmaceutically acceptable and substantially non-toxic in the amounts employed. The dosage form may be a sustained-release preparation. Other dosage forms can include surfactants or other adjuvants. Liquid compositions for topical use can be applied from absorbent pads or be impregnated on bandages and other dressings. Thickeners, such as synthetic polymers, fatty acids, fatty acid salts and esters, fatty alcohols, modified celluloses or modified mineral materials, can be employed with liquid carriers.

PGUs may be in the free base form or in the form of an acid salt thereof. In some embodiment, compounds as described herein may be in the form of a pharmaceutically acceptable salt, which are known in the art (Berge S. M. et al., *J. Pharm. Sci.* (1977) 66(1):1-19). Pharmaceutically acceptable salt as used herein includes, for example, salts that have the desired pharmacological activity of the parent compound (salts which retain the biological effectiveness and/or properties of the parent compound and which are not biologically and/or otherwise undesirable). The acid salts can be generated with any pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Salts, as described herein, may be prepared by conventional processes known to a person skilled in the art, for example, and without limitation, by combining the free form with an organic acid or cation exchange from other salts. Those skilled in the art will appreciate that preparation of salts may occur in situ during isolation and purification of the compounds or preparation of salts may occur by separately reacting an isolated and purified compound.

In embodiments of the invention, PGUs may be in the form of a solvate. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol. In some embodiments of the invention, repeating units of the PGUs can be mixtures of isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience. The PGUs can be stereoregular or random polymers. The PGUs can be copolymers of various repeating units. The copolymers can be block copolymers, random copolymers, dendritic copolymers, or any other form of copolymers.

PGUs or pharmaceutical compositions for use as described herein may be administered by means of a medical device or appliance such as an implant, graft, prosthesis, stent, etc. Also, implants may be devised which are intended to contain and release such compounds or compositions. An example would be an implant made of a polymeric material adapted as a vehicle to release the PGUs over a period of time.

An "effective amount" of a PGU pharmaceutical composition includes a therapeutically effective amount or a prophylactically effective amount. A "therapeutically effective amount" refers to an amount effective, at dosages and for periods of time necessary, to achieve the desired therapeutic result. A therapeutically effective amount of a PGU formulation may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result. Typically, a prophylactic dose is used in subjects prior to the disease, so that a prophylactically effective amount may be less than a therapeutically effective amount.

Dosage values may vary with the severity of the condition to be alleviated. For any particular subject, specific dosage regimens may be adjusted over time according to the individual need and the professional judgment of the person administering or supervising the administration of the compositions. Dosage ranges suggested herein are exemplary only and do not limit the dosage ranges that may be selected by medical practitioners. The amount of PGUs in the composition may vary according to factors such as the disease state, age, sex, and weight of the subject. Dosage regimens may be adjusted to provide the optimum therapeutic response.

In general, PGUs should be used without causing substantial toxicity. Toxicity of the PGUs can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be appropriate to administer substantial excesses of the compositions. PGUs may be administered to a subject, where the "subject" may be a human, non-human primate, rat, mouse, cow, horse, pig, sheep, goat, dog, cat, or any other animal.

Methods and Materials

Synthesis of Guanidine-Containing Aryl Halide Monomer A

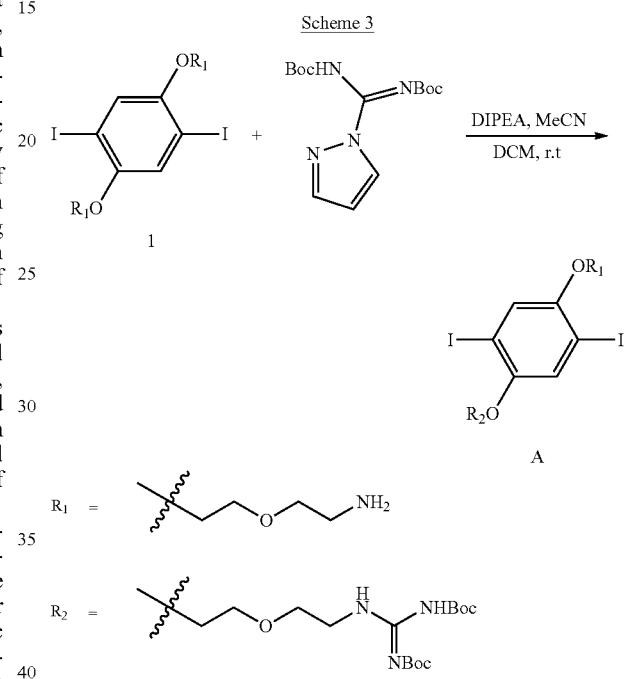

Synthesis of Guanidine-Containing Aryl Halide Monomer A

A 100 mL round bottom flask (RBF) was filled with compound 1 (1.00 g, 1.87 mmol) (synthesized according to literature procedure[1]) and N,N'-Di-Boc-1H-pyrazole-1-carboxamide (1.16 g, 3.73 mmol) under nitrogen atmosphere. A mixture of di-isopropylethylamine (DIPEA), acetonitrile and DCM (1:3.5:7.5 v/v, 20.0 mL) was degassed with $N_2$ flow for 10 min and transferred into the reaction flask via a cannula. The reaction mixture was stirred at room temperature overnight and was then quenched with water before the two layers were separated. The aqueous layer was extracted with DCM, and the combined organic layers were washed with brine, filtered, and concentrated in vacuo. Column chromatography under 30% of ethyl acetate in hexane yielded monomer A as a white powder (1.53 g, 80% yield). $^1$H NMR (400 MHz, CDCl$_3$, δ): 11.5 (s, 1H), 8.67 (t, 11H, J=5.3 Hz), 7.22 (s, 1H), 4.10 (t, 2H, J=4.4 Hz), 3.88 (t, 2H, J=5.2 Hz), 3.78 (t, 2H, J=4.6 Hz), 3.67 (t, 2H, J=5.2 Hz), 1.49 (s, 9H), 1.45 (s, 9H). $^{13}$C NMR (400 MHz, δ): 163.0, 155.4, 152.5, 152.0, 122.7, 86.8, 82.9, 78.1, 69.7, 68.6, 68.5, 28.0, 27.6. FT-IR (neat): 3329, 2978, 2929, 2851, 1719, 1665, 1639, 1614, 1573, 1516, 1482, 1466, 1406, 1394, 1326, 1276, 1242, 1155, 1125, 1048, 1024 cm$^{-1}$. HRMS (ESI+, m/z): [M+H$^+$]. Calcd. For $C_{36}H_{58}I_2N_6O_{12}$, 1021.2275; found, 1021.2008.

Synthesis of Boc-Protected Antimicrobial
Poly(Guanylurea)s (PGUs)

Scheme 4

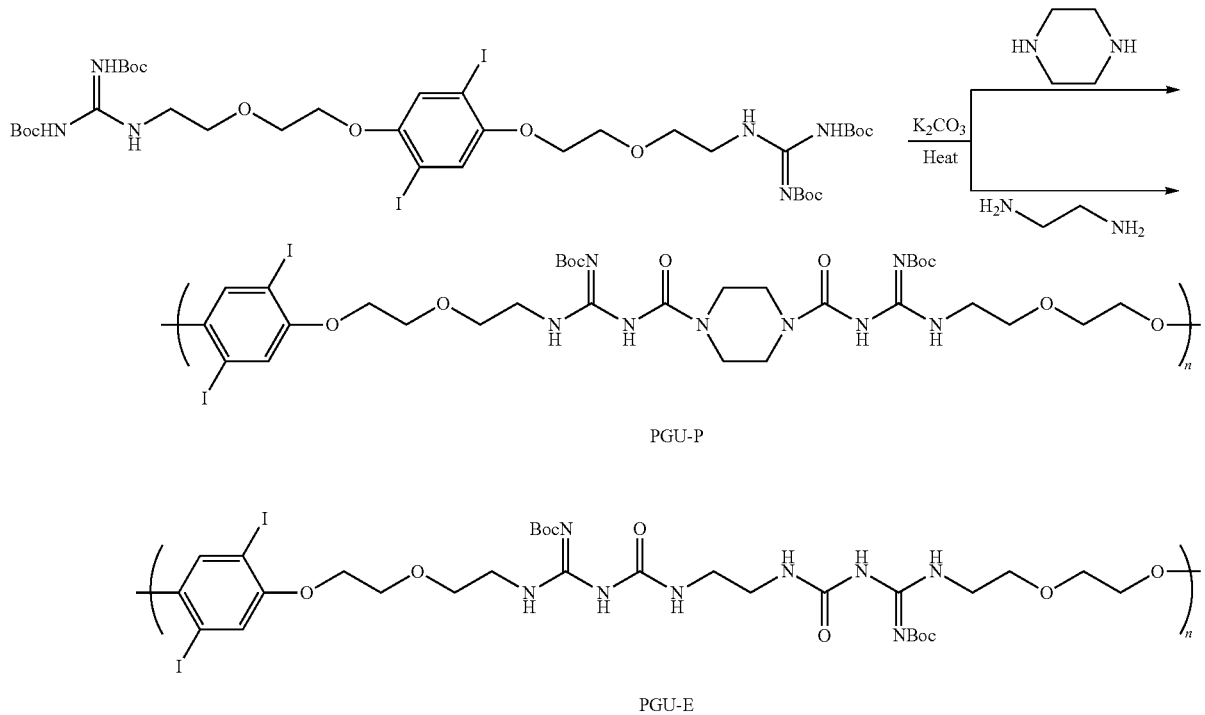

PGU-P

PGU-E

Synthesis of Boc-Protected PGU-P

A Schleck flask was charged with 20.0 mg (0.02 mmol) of Boc-protected guanidine containing di-iodo monomer A, 1.94 mg (0.02 mmol) of piperazine, and 0.14 mg of potassium carbonate ($K_2CO_3$) (0.001 mmol). Then, 0.52 mL of anhydrous tetrahydrofuran (THF) was added and the Schleck flask was degassed for 1 min using $N_2$ bubbling. The reaction mixture was then stirred in a pre-set oil bath at 70° C. for 16 h under nitrogen environment. A viscous polymer solution was filtered through a wool filled glass pipette to remove $K_2CO_3$. The filtrate in THF was precipitated in diethyl ether (1×) and the white fibrous solid was collected by decantation of the solvent. The precipitates were re-dissolved in minimum amount of dichloromethane (DCM) and re-precipitated in methanol (3×). The final polymer was a white gel after drying in high vacuum (12.5 mg, 62% yield). $^1$H NMR (400 MHz, $CDCl_3$, δ): 12.2 (s, 1H), 8.34 (t, 1H, J=4.8 Hz), 7.22 (s, 1H), 4.10 (t, 2H, J=4.6 Hz), 3.88 (t, 2H, J=4.6 Hz), 3.78 (t, 2H, J=5.1 Hz), 3.73 (br s, 2H), 3.60 (q, 2H, J=5.3 Hz, J=5.1 Hz), 3.53 (br s, 2H), 1.44 (s, 9H). FT-IR (neat): 3280, 2938, 1668, 1535, 1483, 1448, 1346 cm$^{-1}$. GPC: Mw=27,500 g/mol, Mn=14,500, g/mol. PDI=1.90.

Synthesis of Boc-Protected PGU-E

A Schlenk flask was charged with 20.0 mg (0.02 mmol) of Boc-protected guanidine containing di-iodo monomer A, 1.35 mg (0.02 mmol) of ethylenediamine, and 0.14 mg of $K_2CO_3$ (0.001 mmol). Then, 0.52 mL (by volume) anhydrous THF solvent was added and the Schleck flask was degassed for 1 min using $N_2$ flow. The reaction was then stirred in a pre-set oil bath at 70° C. for 16 h and equipped with a nitrogen filled balloon. A viscous polymer solution was filtered through a wool filled glass pipette to remove $K_2CO_3$. The filtrate in THF was precipitated in diethyl ether (1×) and a white fiber like powder was collected by decantation of the solvent. The powder was then re-dissolved in minimum amount of DCM and re-precipitated in methanol (3×) to have a pure product. The final polymer was a white gel after drying in high vacuum (12.9 mg with 66% yield). $^1$H NMR (400 MHz, $CDCl_3$, δ): 12.0 (s, 1H), 8.29 (s, 1H), 7.21 (s, 1H), 5.60 (br s, 1H), 4.10 (t, 2H, J=4.1 Hz), 3.96 (t, 2H, J=3.8 Hz), 3.86 (t, 2H, J=4.8 Hz), 3.8 (m, 2H), 3.56 (m, 2H), 3.54 (m, 2H), 3.31 (m, 2H), 1.44 (s, 9H). FT-IR (neat): 3405, 2532, 2159, 2034, 1662, 1437 cm$^{-1}$. GPC: Mw=21, 400 g/mol, Mn=11,200 g/mol, PDI=1.90.

TABLE 2

Properties of Antimicrobial Poly(guanylurea) PGU-P and PGU-E

| PGU | n[a] | Mn (g/mol)[b] | PDI[c] | Yield (%) | HD (nm)[d] |
|---|---|---|---|---|---|
| P-14K | 14 | 14,500 | 1.9 | 62 | 128 ± 0.5 |
| P-8K | 8 | 8,700 | 1.5 | 60 | 86 ± 1.9 |
| P-3K | 3 | 3,100 | 2.5 | 65 | 102 ± 3.7 |
| E-11K | 11 | 11,200 | 1.9 | 66 | 125 ± 3.6 |
| E-7K | 7 | 7,500 | 1.9 | 65 | 106 ± 5.7 |

[a] Degree of polymerization.
[b] Determined by gel permeation chromatography in THF.
[c] PDI (polydispersity index) = $M_w/M_n$.
[d] The average hydrodynamic diameters of three independent samples in 7H9 medium.

Boc-Deprotection of Antimicrobial Poly(Guanylurea)s

Scheme 5

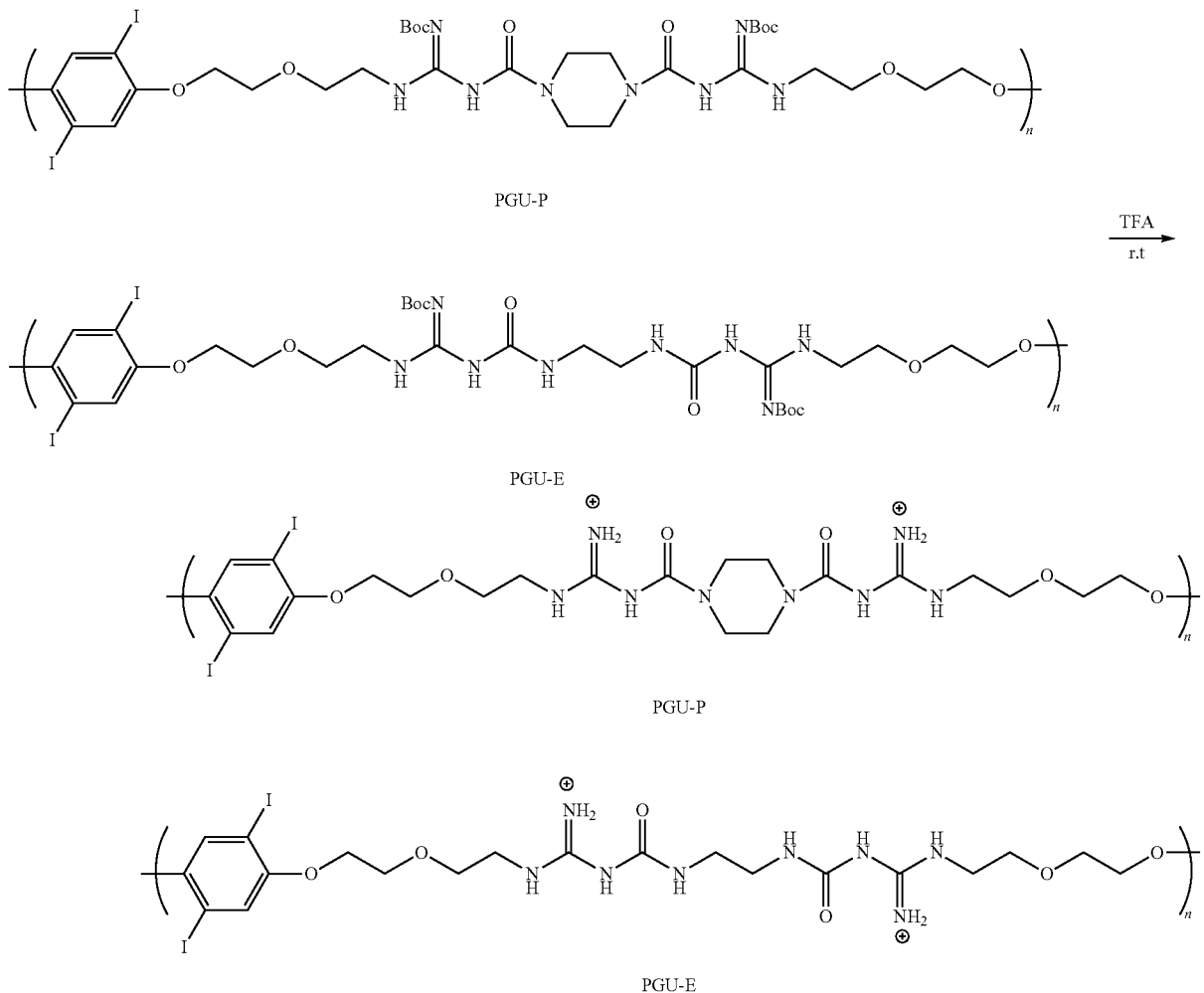

Boc-Deprotection of PGUs

In a vial, a solution of Boc-protected polymer in DCM (1.00 mL) was treated with trifluoroacetic acid (TFA) at room temperature for 24 h. The solvent was removed under reduced pressure and the crude was dissolved in minimum amount of dimethylformamide (DMF) to make a clear homogeneous solution. The polymer in DMF was precipitated in diethyl ether (1×) and the white fiber like powder was collected after decantation of the solvent. The powder was then dissolved in DMF to make a clear solution and re-precipitated in ethyl acetate (EA) (2×) for final purification. The final Boc-deprotected polymer was collected by decantation of the solvent and dried in high vacuum for 24 h.

PGU-P: Using the general procedure described above, the final Boc-deprotected polymer was a white gel like powder (66% yield). $^1$H NMR (400 MHz, DMSO-$d_6$, δ): 10.4 (s, 1H), 9.13 (s, 1H), 8.61 (s, 1H), 7.38 (s, 1H), 4.11 (s, 2H), 3.80 (s, 2H), 3.71 (s, 2H), 3.53 (s, 4H), 3.50 (s, 2H), 3.40 (br s, 2H), 3.38 (br s, 2H) 7. FT-IR (neat): 3360, 2160, 1737, 1681, 1437, 1317 cm$^{-1}$ PGU-E: Using the general procedure described above, the final Boc-deprotected polymer was a white gel like powder (62% yield). $^1$H NMR (400 MHz, DMSO-$d_6$, δ): 10.56 (s, 1H), 9.11 (s, 1H), 8.52 (s, 2H), 7.65 (s, 1H), 7.36 (s, 1H), 4.11 (s, 2H), 3.79 (s, 2H), 3.70 (s, 2H), 3.20 (s, 2H). FT-IR (neat): 3280, 2938, 1668, 1534, 1483, 1448, 1346 cm$^{-1}$ Measurement of Hydrodynamic Diameter Single particle light scattering analysis, also known as nanoparticle tracking analysis (NTA) was utilized to measure the hydrodynamic diameter of antimicrobial poly(guanylurea)s, exemplary results of the measurements are shown in FIGS. 2A-2F. Compared to DLS, NTA gives a more accurate representation of the particle with a broad size distribution, because of the direct detection of each nanoparticle. A 50 μM stock solution of polymer in DMSO was prepared. 50 μL of the stock polymers was diluted with 950 μL of PBS (pH 7.4). The final concentration of the polymer solution was 2.5 μM (5% DMSO and 95% PBS). The sample solution was then injected to a sample chamber of NTA for data acquisition for 90 seconds. All measurements were performed in triplicate at 25° C. using a temperature controller and the average value was reported.

Hemolysis Assay

The hemolysis assay was carried out using fresh human RBCs purchased from Zenbio, Inc., without further processing. The RBCs were diluted to 2% (v/v) RBCs in TBS (pH 7.4, 0.01 M Tris-HCl, 0.155 M NaCl). Stock polymer solutions were prepared in dimethyl sulfoxide (DMSO) at 8 mg/mL and diluted with TBS to give a working solution of 8000 μg/mL. Serial dilutions were made in a 96-well plate (Bio-One, Cellstar, Greiner) so that concentrations were stepwise halved eight times to give a range from 4,000 μg/mL to 31.25 μg/mL in 50 μL TBS. Later, 10 μL of 1 mg/mL stock solution of the hemolytic compound triton X-100 was added to 40 μL TBS as a positive control, 50 μL TBS as control (blank), and 100 μL TBS as background control. Finally, 50 μL of the 2% RBC solution was added to each well containing a 50 μL sample or a control. The plate was shaken gently for 1 min then incubated for 1 h at 37° C. Thereafter, the plate was centrifuged at 400 g for 5 min, subsequent to which 50 μL of the supernatant was pipetted into a new 96-well plate, and the optical density (OD) was measured at 414 nm on a UV-Vis plate reader. For statistical analysis, blank $OD_{414}$ values were subtracted from both sample $OD_{414}$ and positive control $OD_{414}$ values. $OD_{414}$ was normalized to 100% with the lowest $OD_{414}$ assigned to 0% hemolysis, and the triton X-100 positive control assigned to 100% hemolysis. The data was plotted as $OD_{414}$ vs. $\log_{10}$ of the concentration using the graphing software Graphpad Prism. A sigmoidal curve was fitted to the data by the software to yield $HC_{50}$ values and 95% confidence intervals. The $HC_{50}$ values shown in FIGS. 3A-3D, are the average values derived from three replicates of hemolysis experiments, and error bars represent the standard error of the mean.

MTT Assay

The cell viability assay was conducted using 3000 Hela cells per well in a complete medium. The cells (200 μL of 15,000 cells/mL) were seeded into a 96 well plate and incubated for 16 h to 24 h until reaching 60% confluency in 5% $CO_2$ at 37° C. The antimicrobial polymer samples were prepared by serial dilution of 5 mM stock polymer in DMSO to prepare 0.5, 1.0, 2.0 and 4.0 mM, respectively, in DMSO. Polymer solutions were further diluted 10 times in water to make working concentrations of 50, 100, 200 and 400 μM, respectively. Then, 20 μL of each diluted polymer samples were added to each well with 180 μL complete medium in triplicate and incubated for 24 h. Later, 10 μL of MTT (12 mM) solution was added into each well and further incubated for 4 h according to the manufacturer's protocol. After the existing media was discarded, 50 μL DMSO was added to each of the wells and shaken for 30 min. Absorbance of each well was measured by microplate well reader at 570 nm and cell viability was reflected by the ratio between the absorbance of treated and control cells. Three repeats were conducted for each sample.

Figure 4:
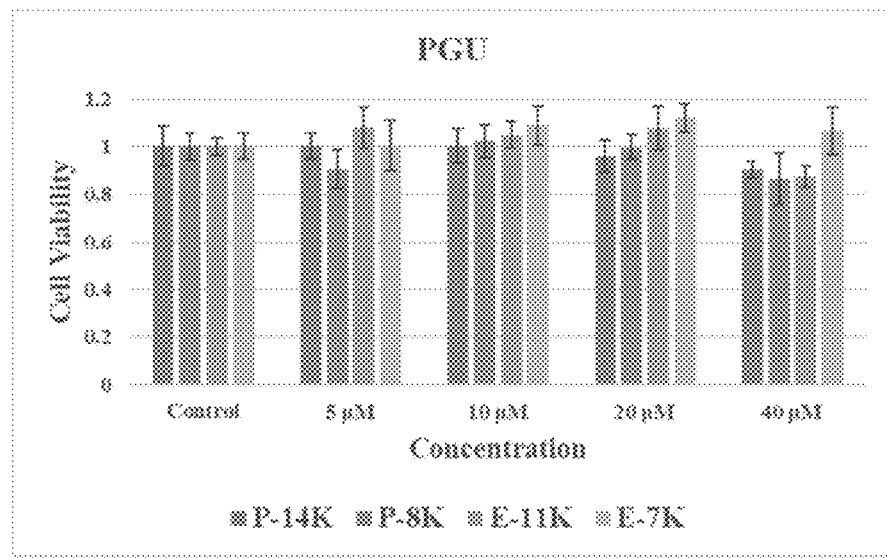
FIG. 4 shows a bar chart of the cell viability of various PGU, according to an embodiment of the invention, by MTT assay.

Antimicrobial assay antimicrobial activities of the polymers were determined by the minimal inhibitory concentration (MIC) assay. MIC of *Mycobacterium smegmatis* (ATCC 700084), *Shigella flexneri* (ATCC 9199), *Staphylococcus aureus* (ATCC 14775) and methicillin-resistant *Staphylococcus aureus* (MRSA) (ATCC BAA-44) were determined by the standard broth microdilution method with slight modification. In brief, different bacteria were grown in either Mueller Hinton broth (MHB) or 7H9 broth (*M. smegmatis*) overnight at 37° C. Next day, the cells were first $OD_{600}$ adjusted to 0.1 and then further diluted 1:100 in the respective media and 50 μL (~$10^5$ CFU) is added to 96 well-microplate wells containing 50 μL serial dilutions of the polymers. The plates were incubated for 20-44 h at 37° C. MIC is defined as the lowest concentration of the polymer that inhibits the visual growth of the bacteria. To aid in determining the visual growth of bacteria, resazurin, a red-ox dye is added to the wells at a final concentration of 0.02% and incubated for 4-8 h at 37° C. In the presence of viable cells, resazurin (blue) is reduced to resorfurin (pink) along with an increase in fluorescence. MIC was calculated as the lowest concentration of the polymer that prevented the color change and reduced the fluorescence (Ex 540, Em 590 nm) by 90% when compared to the control wells containing no inhibitor. Ciprofloxacin was used as a positive control for bacterial growth inhibition. The MIC assays were repeated at least three times and the most consistent results are shown in FIG. 4.

Antimicrobial Mechanism Study

Figure 5:
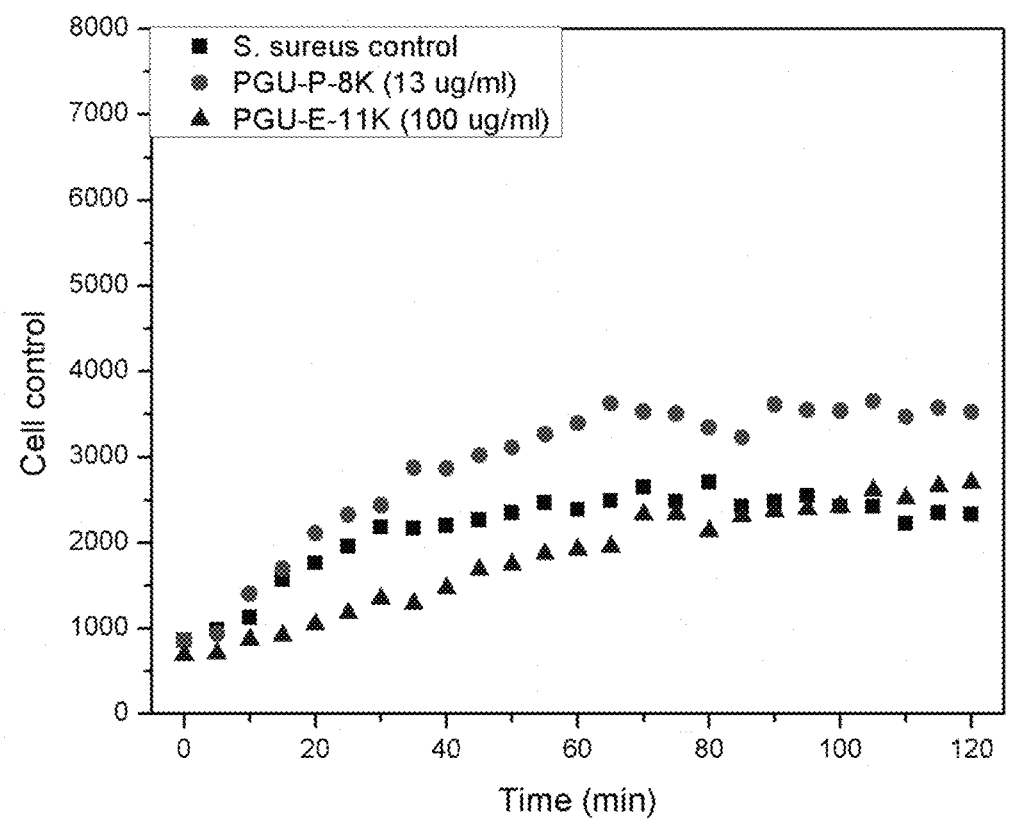
FIG. 5 shows plots of the rate of membrane permeation and nucleic acids intercalation for control EB (rectangles) and various PGU-treated cells, according to embodiments of the invention, (circles and triangles), which allow high EB internalization caused by the membrane disruption of *S. aureus* as indicated by fluorescence.

Ethidium bromide accumulation assay was performed according to a modified protocol followed in many other studies. In brief, log phase cells of *M. smegmatis* or other bacterial species grown in 7H9 broth or MHB respectively were centrifuged, washed and re-suspended in PBS buffer or PBST (PBS buffer containing 0.05% tween 80, for *M. smegmatis*) to an $OD_{600}$ of 0.2. Aliquots (50 μL) of the cell suspension was added to black microtiter plate wells each containing 50 μL of the serially (2 fold) diluted polymers. Highest concentration tested was usually the MIC concentration relevant for the particular bacteria/polymer combination. Ethidium bromide (EB) was added to each well at a final concentration of 2.5 μM. Fluorescence (Ex 540, Em 590) was then measured (every 3 min) in a plate reader for 1-2 h at 37° C. Results for *S. flexneri*, FIG. 1, and *S. aureus*, FIG. 5 are provided. Verapamil, an efflux pump inhibitor was used as an assay control to verify the increase in ethidium bromide fluorescence.

All publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A poly(guanylurea) (PGU), comprising the structure:

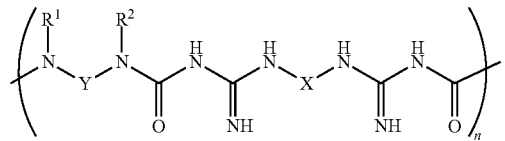

or any protonated or plurally protonated salt thereof

Where: n is 3 to 100; X is linear or cyclic alkylene, heteroatom interrupted alkylene, cycloalkylene, arylene, heteroarylene, or a combination thereof; Y is linear or cyclic alkylene, one or more heteroatom interrupted alkylene where the heteroatom is O, S, NH, or a combination thereof, cycloalkylene, arylene, heteroarylene, or a combination thereof; and $R^1$ and $R^2$ are independently, H, substituted or unsubstituted linear, branched, or cyclic alkyl, one or more heteroatom interrupted substituted or unsubstituted linear branched or cyclic alkyl where the herteroatom is O, S, NH or a combination thereof, unsubstituted or substituted aryl, substituted or unsubstituted heteroarylene; or $R^1$ and $R^2$ are combined as an alkylene or heteroatom interrupted alkylene, where $R^1NYNR^2$ comprises a dinitrogen heterocycle, and where substituents are $C_1$ to $C_{20}$ alkyl, $C_1$ to $C_{20}$ alkoxy, hydroxyl, $C_1$ to $C_{20}$ acyl, $C_1$ to $C_{20}$ acyloxy, amino, $C_1$ to $C_{20}$ alkyl amino, $C_1$ to $C_{20}$ dialkylamino, $C_1$ to $C_{20}$ acylamino, $C_2$ to $C_{20}$ acylalkylamino, fluoro, chloro, bromo, iodo, mercapto, $C_1$ to $C_{20}$ alkylthio, $C_6$ to $C_{18}$ aryl, $C_6$ to $C_{18}$ aryloxy, $C_6$ to $C_{18}$ arylamino, $C_6$ to $C_{32}$ diarylamino, or $C_7$ to $C_{38}$ alkylarylamino.

2. The PGU according to claim 1, wherein the structure is:

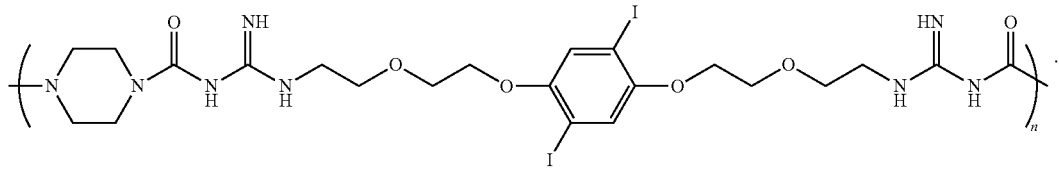

3. The PGU according to claim 1, wherein the structure is:

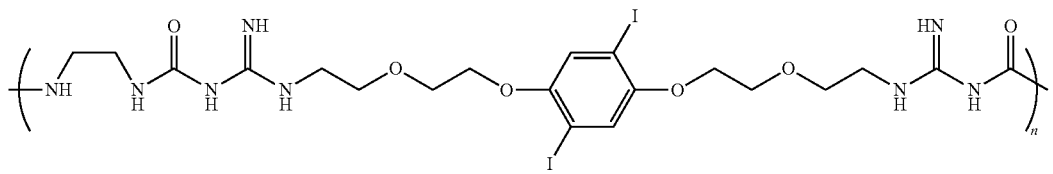

4. The PGU according to claim 1, wherein X comprises an arylene, a cycloalkylene, a heterocycle.

5. The PGU according to claim 1, further comprising at least one tert-butyloxycarbonyl protecting group (BOC).

6. A method of making a PGU, according to claim 1, comprising:
providing a first monomer comprising a di-terminal Boc-protected guanidine monomer comprising a linear or cyclic alkylene, heteroatom interrupted alkylene, cycloalkylene, arylene, heteroarylene, or a combination thereof;
providing a second monomer comprising: an isocyanate; or a dinitrogen heterocycle with a carbonate; or a diamine capped linear or cyclic alkylene, one or more heteroatom interrupted alkylene where the herteroatom is O, S, NH, or a combination thereof with the carbonate;
combining the first and second monomer in a solvent as a solution;
heating the solution; and
isolating the PGU.

7. The method according to claim 6, wherein the second monomer is a dinitrogen heterocycle.

8. The method according to claim 6, wherein the carbonate is an alkali metal carbonate.

9. A pharmaceutical composition comprising a PGU according to claim 1, wherein the PGU is the protonated or plurally protonated salt thereof.

10. The pharmaceutical composition according to claim 9, wherein the protonated or plurally protonated salt is the salt of acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid.

11. The pharmaceutical composition according to claim 9, wherein the pharmaceutical composition is an antimicrobial agent.

12. The PGU according to claim 1, wherein the PGU is in the form of a nanoparticle.

13. The PGU according to claim 12, wherein the nanoparticle has a narrow size distribution.

* * * * *